US011832834B2

(12) United States Patent
Hogan et al.

(10) Patent No.: US 11,832,834 B2
(45) Date of Patent: Dec. 5, 2023

(54) POSITIONING GUIDE SYSTEM WITH SENSOR

(71) Applicant: 360 Knee Systems Pty Ltd, New South Wales (AU)

(72) Inventors: Jason Keith Hogan, New South Wales (AU); Willy Theodore, New South Wales (AU); Brad Peter Miles, New South Wales (AU); Peter Bede O'Connor, New South Wales (AU)

(73) Assignee: 360 Knee Systems Pty Ltd, New South Wales (AU)

( * ) Notice: Subject to any disclaimer, the term of this patent is extended or adjusted under 35 U.S.C. 154(b) by 685 days.

(21) Appl. No.: 15/740,200

(22) PCT Filed: Jul. 1, 2016

(86) PCT No.: PCT/AU2016/050580
§ 371 (c)(1),
(2) Date: Dec. 27, 2017

(87) PCT Pub. No.: WO2017/004669
PCT Pub. Date: Jan. 12, 2017

(65) Prior Publication Data
US 2018/0177512 A1 Jun. 28, 2018

(30) Foreign Application Priority Data
Jul. 3, 2015 (AU) ................... 2015902628

(51) Int. Cl.
*A61B 17/17* (2006.01)
*A61B 17/15* (2006.01)
*A61B 17/56* (2006.01)

(52) U.S. Cl.
CPC ........ *A61B 17/1764* (2013.01); *A61B 17/155* (2013.01); *A61B 17/157* (2013.01);
(Continued)

(58) Field of Classification Search
CPC ............ A61B 17/17645; A61B 17/155; A61B 17/157; A61B 17/158; A61B 2562/0247; A61B 2562/0257; A61B 2017/568
(Continued)

(56) References Cited

U.S. PATENT DOCUMENTS 8,491,589 B2 * 7/2013 Fisher .................... A61B 17/02
606/88
8,718,820 B2 * 5/2014 Amiot .................. A61B 17/157
606/88
(Continued)

FOREIGN PATENT DOCUMENTS

WO     2015/057814 A1    4/2015

OTHER PUBLICATIONS

"International Search Report" issued in PCT/AU2016/050580, dated Sep. 7, 2016, 10 pages.
(Continued)

*Primary Examiner* — Marcela I. Shirsat
(74) *Attorney, Agent, or Firm* — Nixon Peabody LLP

(57) ABSTRACT

A positioning guide system for guiding a surgical tool comprising a positioning guide and a user interface. The positioning guide comprising: an interface to correspond to a plurality of anatomic landmarks of a patient; a plurality of sensors to provide an output indicative of the proximity of the interface and one or more of the plurality of anatomic landmarks; and a tool guide, for a surgical tool, positioned relative to the interface. The user interface provides a user output indicative of correct positioning of the positioning guide and the anatomic landmarks of the patient based on the output of the plurality of sensors.

17 Claims, 11 Drawing Sheets

(52) U.S. Cl.
CPC ...... *A61B 17/158* (2013.01); *A61B 2017/568* (2013.01); *A61B 2562/0247* (2013.01); *A61B 2562/0257* (2013.01)

(58) Field of Classification Search
USPC .......................................................... 606/88
See application file for complete search history.

(56) References Cited

U.S. PATENT DOCUMENTS

| | | |
|---|---|---|
| 2004/0146830 A1 | 7/2004 | Weinsten |
| 2004/0243148 A1* | 12/2004 | Wasielewski .......... A61B 5/067 977/932 |
| 2005/0177169 A1* | 8/2005 | Fisher ................... A61F 2/4684 606/88 |
| 2007/0233141 A1* | 10/2007 | Park ..................... A61B 17/155 606/88 |
| 2008/0125785 A1 | 5/2008 | Chana |
| 2010/0249665 A1 | 9/2010 | Roche |
| 2012/0053488 A1* | 3/2012 | Boutin ................... A61B 34/10 600/587 |
| 2015/0088141 A1* | 3/2015 | Uthgenannt ....... A61B 17/1675 623/20.14 |
| 2016/0089153 A1* | 3/2016 | Couture ................. G16H 50/50 606/88 |

OTHER PUBLICATIONS

"International Preliminary Report on Patentability" issued in PCT/AU2016/050580, dated Oct. 23, 2017, 6 pages.

\* cited by examiner

POSITIONING GUIDE SYSTEM WITH SENSOR

CROSS-REFERENCE TO RELATED APPLICATIONS

The present application is a U.S. National Stage of International Application No. PCT/AU2016/050580 filed on Jul. 1, 2016, which claims priority from AU 2015902628 filed on Jul. 3, 2015. Each of these applications is hereby incorporated by reference in its entirety for all purposes.

TECHNICAL FIELD

The present disclosure relates to a positioning guide system for guiding surgical tools.

BACKGROUND

It is important to accurately position surgical tools during surgery to allow the most effective treatment. One example includes surgery in relation to bones and joints, such as knee and hip replacement surgery. This may involve cutting, or otherwise shaping, bone and cartilage of the patient and securing implantable components thereto.

To assist accuracy a positioning guide may be placed relative to anatomic landmarks of the patient. Anatomic landmarks may include portions of the surface of the bone, cartilage and soft tissue constructs. The surgeon may then position surgical tools relative to the positioning guide. The positioning guide may then assist a blade to cut the bone, assist drilling into the bone, assist insertion of pins into the bone, and/or assist positioning and securing an implantable component to the bone.

A positioning guide may be configured (i.e. tailored) for a particular patient. For example, this may involve a CT scan (X-ray computed tomography) or MRI (magnetic resonance imaging) to determine anatomic landmarks of the bone, cartilage and/or soft tissue constructs of the patient. This information may then be used to determine a shape of a positioning guide that can be placed in contact with the bone and cartilage and have one "unique location" (relative to the bone). A positioning guide may then be manufactured for the surgery. The positioning guide may also have slot, apertures or other structural feature to which other surgical tools are indexed.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

A positioning guide system for guiding a surgical tool comprising a positioning guide. The positioning guide comprises: an interface to correspond to a plurality of anatomic landmarks of a patient; and a plurality of sensors to provide an output indicative of the proximity of the interface and one or more of the plurality of anatomic landmarks. The positioning guide also comprises a tool guide, to receive a surgical tool, positioned relative to the interface. The positioning guide system also comprises a user interface to provide a user output indicative of correct positioning of the positioning guide and the anatomic landmarks of the patient based on the output of the plurality of sensors.

The positioning guide system may advantageously provide the user feedback, in the form of the user output, to inform the user that the positioning guide is correctly positioned. This may be in contrast with known positioning guides where the user may confirm correct positioning by feeling for movement between the positioning guide and the bone of the patient. The user output from the presently disclosed positioning guide system may be more objective, faster and accurate.

The positioning guide system may further comprise a plurality of recesses at the interface to receive the plurality of sensors. The plurality of sensors may be mounted to the interface. The sensors may be removable. This may allow sensors to be removed, sterilised and reused with another positioning guide.

In the positioning guide system, the sensors may include pressure sensors wherein the output is indicative of pressure between the interface and the anatomic landmarks.

In the positioning guide system, the sensors may include proximity sensors wherein the output is indicative of distance between the interface and the anatomic landmarks.

The positioning guide may include one or more guide apertures to receive a surgical tool. The guide apertures may guide the surgical tool by limiting movement or providing a limited range of movement.

In the positioning guide system, the user output may include one or more of a visual, audio and haptic output. The user interface may be mounted to the positioning guide. The user interface mounted on the positioning guide may provide a convenient means for the user to receive the user output.

In the positioning guide, the interface may comprise one or more contoured surfaces. In the positioning guide, the contoured surface is contoured to correspond to anatomic landmarks on a femur, tibia or patella of the patient.

In the positioning guide, the interface may correspond to a plurality of anatomic landmarks where the plurality of anatomic landmarks comprise features of a first bone, cartilage and/or soft tissue constructs of the patient.

The tool guide may provide a reference for the surgical tool relative to the first bone, cartilage and/or soft tissue constructs of the patient. That is, guiding the surgical tool to the bone, cartilage and/or soft tissue constructs having the anatomic landmarks. The tool guide may further provide a reference for the surgical tool relative to a second bone, cartilage and/or soft tissue constructs of the patient.

The positioning guide may also include a second interface to correspond to second anatomic landmarks, separate to the said anatomic landmarks, wherein correct positioning of the positioning guide further comprises positioning the second interface relative to the second anatomic landmarks. The second anatomic landmarks may also be part of an anatomy of a patient, such another bone, cartilage and/or soft tissue constructs. This may be useful in instances where positioning guide, and the surgical tool, needs to be guided relative to another bone, cartilage and/or soft tissue constructs.

The second anatomic landmarks may include a prepared surface of a further bone, cartilage and/or soft tissue constructs.

There is also disclosed a positioning guide for guiding surgical tools, the positioning guide comprising: an interface to correspond to a plurality of anatomic landmarks on bone, cartilage and/or soft tissue constructs of a patient; and a plurality of sensors to provide an output indicative of the proximity of the interface and one or more of the plurality of anatomic landmarks. A tool guide, to receive a surgical tool, is positioned relative to the interface.

There is also disclosed a positioning guide for guiding surgical tools, the positioning guide comprising: an interface to correspond to a plurality of anatomic landmarks on bone, cartilage and/or soft tissue constructs of a patient; and a plurality of recesses at the interface to receive a plurality of sensors, wherein the recesses are located to correspond to the plurality of anatomic landmarks. A tool guide, to receive a surgical tool, is positioned relative to the interface.

The interface of the positioning guide may comprise a contoured surface. The contoured surface may have a surface that corresponds to a surface having the anatomic landmarks.

BRIEF DESCRIPTION OF DRAWINGS

Examples of the present disclosure will be described with reference to.

DESCRIPTION OF EMBODIMENTS

Overview

Figure 1:
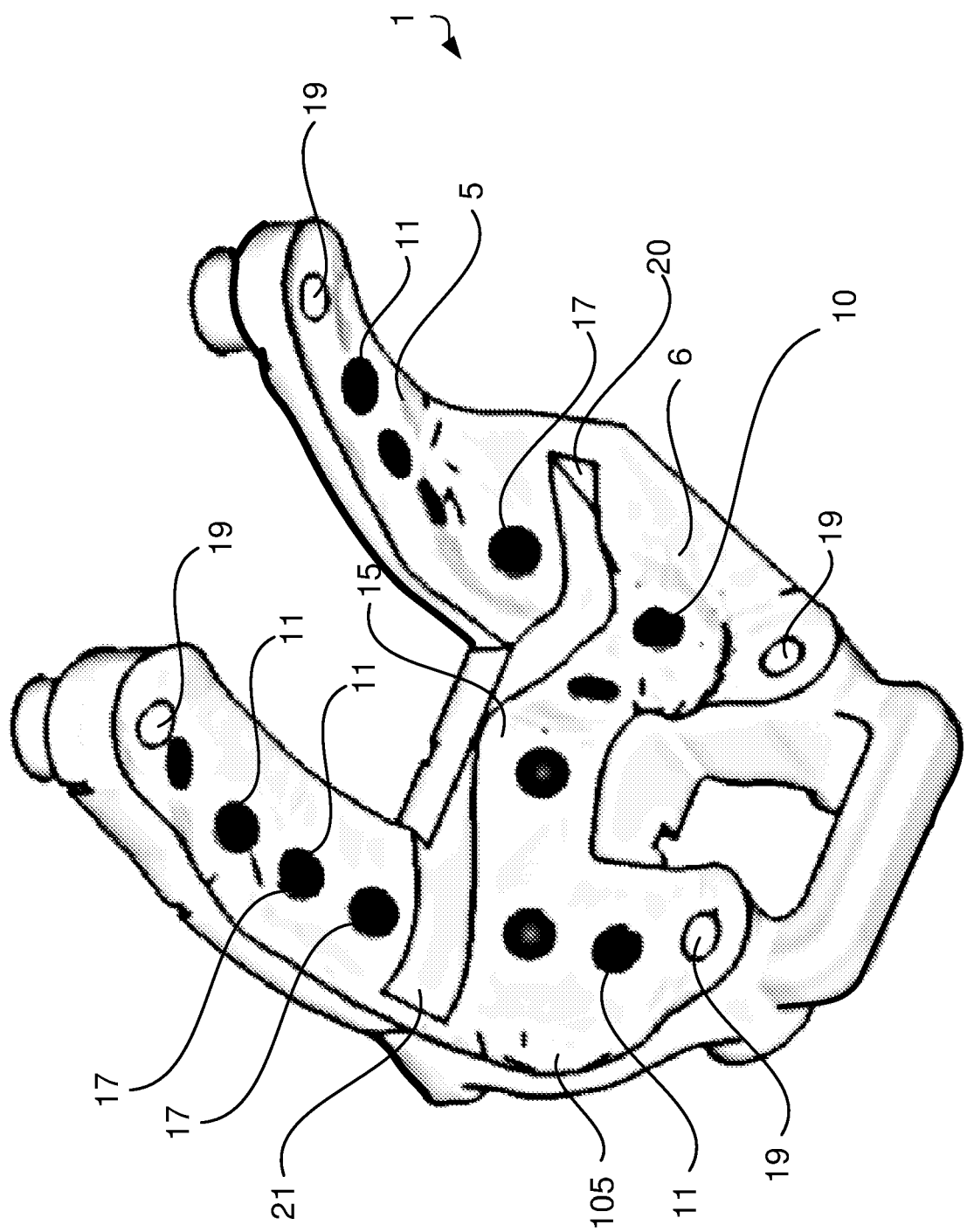
FIG. 1 illustrates a perspective view of a positioning guide for a femur.
Figure 2:
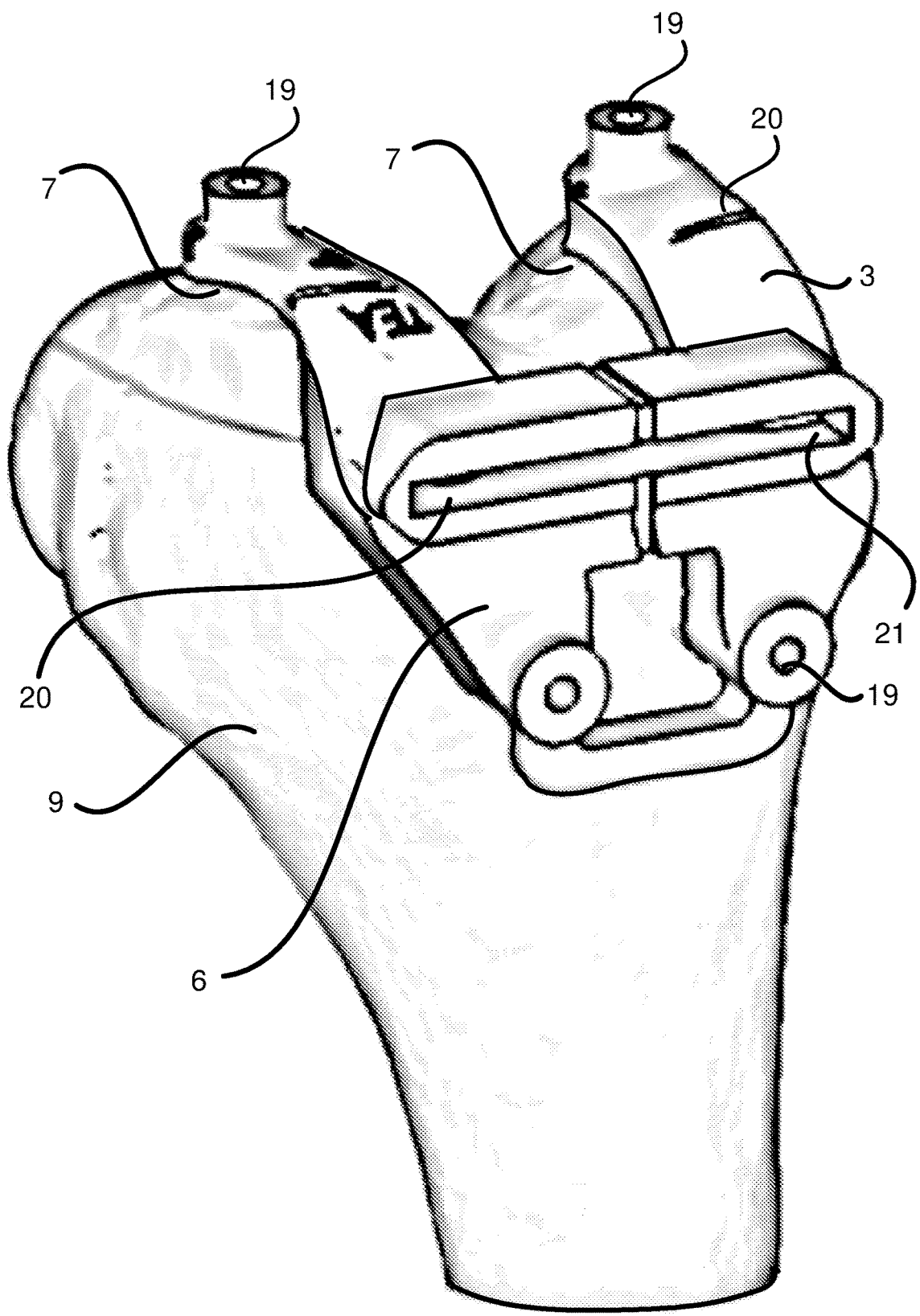
FIG. 2 illustrates a perspective view of the positioning guide in FIG. 1 positioned with a femur.

FIGS. 1 and 2 illustrate a positioning guide system 1 for guiding a surgical tool. The positioning guide system includes a positioning guide 3 that has an interface 5 to correspond to a plurality of anatomic landmarks 7 of a patient. This is illustrated in FIG. 2 where the positioning guide 3 is positioned relative to anatomic landmarks 7 on bone 9 and/or cartilage, such as an end of a femur bone 9 of the patient. A plurality of sensors 11 provide an output indicative of the proximity of the interface 5 and one or more of the plurality of anatomic landmarks 7. The positioning guide 3 also includes a tool guide 20, for a surgical tool, positioned relative to the interface 5. The positioning guide system 1 also includes a user interface 13 (see FIG. 3) to provide a user output 15 indicative of correct positioning of the positioning guide 3 and the anatomic landmarks of the patient based on the output of the plurality of sensors 11.

This allows the user, such as a surgeon, to be notified that the positioning guide 3 has been positioned at the desired position relative to the bone 9 and/or cartilage. This may be advantageous since it may be difficult for the surgeon to visually inspect that the interface 5 is positioned correctly relative to the anatomic landmarks 7. For example, the area may be obscured by human tissue and/or by the remaining portions of the positioning guide 3. In known positioning guides, the user may need to tactilely move the positioning guide until the user does not feel gaps between interface 3 and the anatomic landmarks 7. This may take time and correct positioning may be dependent on the skill of the user. This is in contrast to the positioning guide system 1 which may assist the user to accurately position the positioning guide 3 by providing an objective user output to indicate correct positioning.

The positioning guide system 1 may have application for a variety of orthopaedic applications. This may include procedures related to bone, cartilage and/or soft tissue constructs. Some specific applications include, but are not limited to, preparation for joint replacement surgery (such as knee, hip and elbow).

Positioning Guide

The features of an example of a positioning guide 3 will now be described in a non-limiting example with reference to FIGS. 1 and 2.

In FIG. 1, the interface 5 is in the form of a contoured surface 105. The contoured surface has a generally concave surface such that the positioning guide 3 may receive the end of the femur bone 9. In use, the interface 5 faces a corresponding surface (having anatomical landmarks 7) of the lower extremity of the femur bone 9. Thus the interface 5 may correspond closely with the corresponding surface of the bone 9 (such as the ridge 15 of the contoured surface that follows a notch in the femur bone 9). Generally, the interface 5 corresponds to a sufficient number of anatomic landmarks 7 of the bone such that there is only one relative configuration between the positioning guide 3 and the bone 9 when the interface 5 is in close proximity (including in physical contact) with all the anatomic landmarks 7. That is, when the positioning guide 3 and bone 9 are uniquely located relative to one another. Ideally, the positioning guide 3 and the bone 9 are uniquely located in position (in the three perpendicular axes) and rotation (in the three perpendicular axes).

The interface 5 is located on a body 6 of the positioning guide 3. The body 6 also includes pin apertures 19 and a tool guide 20 in the form of a guide aperture 21.

The pin apertures 19 allow passage of a pin (not shown) to fasten the positioning guide 3 to the bone 9. In one example, a self-tapping pin (such as a screw) may be inserted through the pin apertures 19. In yet another example, the pin aperture 19 may be used as a guide a drill bit into the bone 9 before insertion of the pin. In yet another example, the pin apertures 19 may be used to guide a surgical tool. For example, the pin apertures 19 may assist in the drill bit (being a surgical tool) to create an aperture in the bone. The aperture in the bone may receive guide pins (not shown) which, when secured to the bone, may be used to guide other surgical tools.

The tool guide 20, in the form of guide aperture 21, in this example is a slot. The guide aperture 21 may receive a blade (not shown) used for cutting and shaping the bone 9. The slot limits the range of motion of the blade so that only the specified portions of bone 9 are cut. The guide aperture 21 may, in other embodiments, be in the form of a circular aperture to receive pins, screws, bolts and other fasteners associated with the surgical tool. It is to be appreciated that the guide aperture 21 is one form of guiding a surgical tool and that guiding surgical tools with a tool guide 20 may be achieved in other ways. For example, in one embodiment, the positioning guide 3 may include a tool guide 20 in the form of one or more indexing surfaces (such as a flange or a stop), whereby the surgical tool is positioned and indexed from that indexing surface.

The positioning guide 3 includes a plurality of recesses 17 at the interface 5 to receive the sensors 11. The recesses 17 may be located on the interface 5 to correspond to the plurality of anatomic landmarks 7. This may allow the sensors 11 to determine the proximity of the interface 5 to the respective anatomic landmarks 7. In one example, the recesses 17 are configured to allow the sensors 11 to be removably mounted. This may include providing threading to the recesses 17 such that the sensors 11 may be fastened to the recess. In other examples, the sensors 11 mounted by interference fit with the recess 17. The recess 17 may further include an aperture through the interface 5 to allow passage of a fastener and/or wire (such as a power or communications wire to the sensor 11).

The positioning guides 3 may be manufactured specifically for a patient. In some examples, a 3D model is built relative to the patient's geometry by parametrically modifying a base model relative to key anatomical landmarks (which may be determined by a CT scan or MRI scan) and a surgical plan. The patient's geometry is then merged into the base model to form a patient specific design.

In one form, additive or subtractive manufacturing techniques may be used to manufacture the positioning guides in accordance with the patient specific design. In one example, the positioning guide 3 may be manufactured from 3D printing technology, such as using selective laser sintering to produce a body 6 of polyamide (nylon). In another example, the body 6 may be manufactured with a CNC milling process. Further examples may include a combination of additive and subtractive manufacturing techniques as well as other manufacturing techniques (such as injection moulding). These processes may be advantageous by providing tailored parts for the particular patient in a cost effective manner.

The positioning guide 3 may be manufactured from materials suitable for sterilisation. In one example, sterilisation includes autoclave sterilisation and the material may be selected from materials suitable for this process. In other examples, sterilisation may include gamma irradiation and the material may be selected from materials suitable for this process. An example of material that may be suitable is a polyaryletherketone offered by EOS GmbH under the trade mark EOS PEEK HP3. Another example of a material that may be suitable is stainless steel, such as those offered by EOS GmbH under the trade mark EOS StainlessSteel GP1, EOS StainlessSteel PH1, EOS StainlessSteel 316L. Yet another example of a material that may be suitable is cobalt chrome, such as those offered by EOS GmbH under the trade mark EOS CobaltChrome MP1. Another example of a material that may be suitable is titanium, such as those offered by EOS GmbH under the trade mark EOS Titanium Ti64ELI. Another example of a material that may be suitable is acetal copolymers, such as that offered by Celanese corporation under the trade marks Hostaform and Celcon. Yet another example of a material that may be suitable is acetal homopolymer, such as those offered by E. I. du Pont de Nemours and Company (DuPont) under the trade mark Delrin.

Sensors

The sensors 11 may include any sensors that can provide an output indicative of proximity of the interface, where the sensor 11 is located, and to the plurality of anatomic landmarks 7, which is generally on the surface of the bone 9 and/or cartilage.

In example, the sensors 11 are pressure sensors where the output is indicative of the pressure between the part of the interface 5, where the sensor 11 is located, and the surface of the bone 9 having the anatomic landmarks 7. In one example, it may be desirable to position the positioning guide 3 so that the output for all the sensors 11 indicate a consistent (non-zero) pressure. This may be indicative of correct positioning of the positioning guide without an unwanted bias to one or more directions. However, it is appreciated that in some other examples, it may be desirable to have an output for the sensors 11 that have different indicative pressures. This may be for instances where correct positioning of the positioning guide 3 require greater pressure in one or more directions. Examples of pressure sensors may include sensors based on piezoresistive effect. Commercial examples of pressure sensors include those offered by Tekscan, Inc. under the trade marks K-Scan and Flexi-Force. Other sensors that may be suitable include pressure catheter sensors offered by Keller AG für Druckmesstechnik.

In other examples, the sensors 11 may include a sensor to detect proximity in the form of contact with the anatomic landmarks 7. This may include using a micro switch to provide an output indicative of contact with the anatomic landmarks 7.

In other examples, the sensors 11 may be in the form of proximity sensors provide an output indicative of distance between the interface, where the sensor 11 is located, and the surface of the bone 9 having the anatomic landmarks 7. In some examples, the proximity sensors are capacitive or photoelectric sensors. The output may be indicative of a distance, or indicative of a particular range of distance, or indicative of a distance above and/or below a specified distance. An example of a proximity sensor is a product offered by OMRON Corporation under the trade mark E2E. Another example of a proximity sensor is a product offered by Omega Engineering Limited under the trade mark Cutler-Hammer Inductive Proximity Sensors, E57. Another example of a proximity sensor is an inductive proximity sensor offered by Pepperl+Fuchs under the model number NBB1-3M22-E0.

In one example, the sensors 11 are removably mounted to the positioning guides 3. This may allow sensors 11 to be sterilised after surgery for use in subsequent surgeries, since the body 6 of the position guides are generally suitable for only one specific patient.

User Interface

The user interface 13 may include any user interface than can provide an output to the user. In some examples, the user interface may provide a visual, audio or haptic output.

Figure 3:
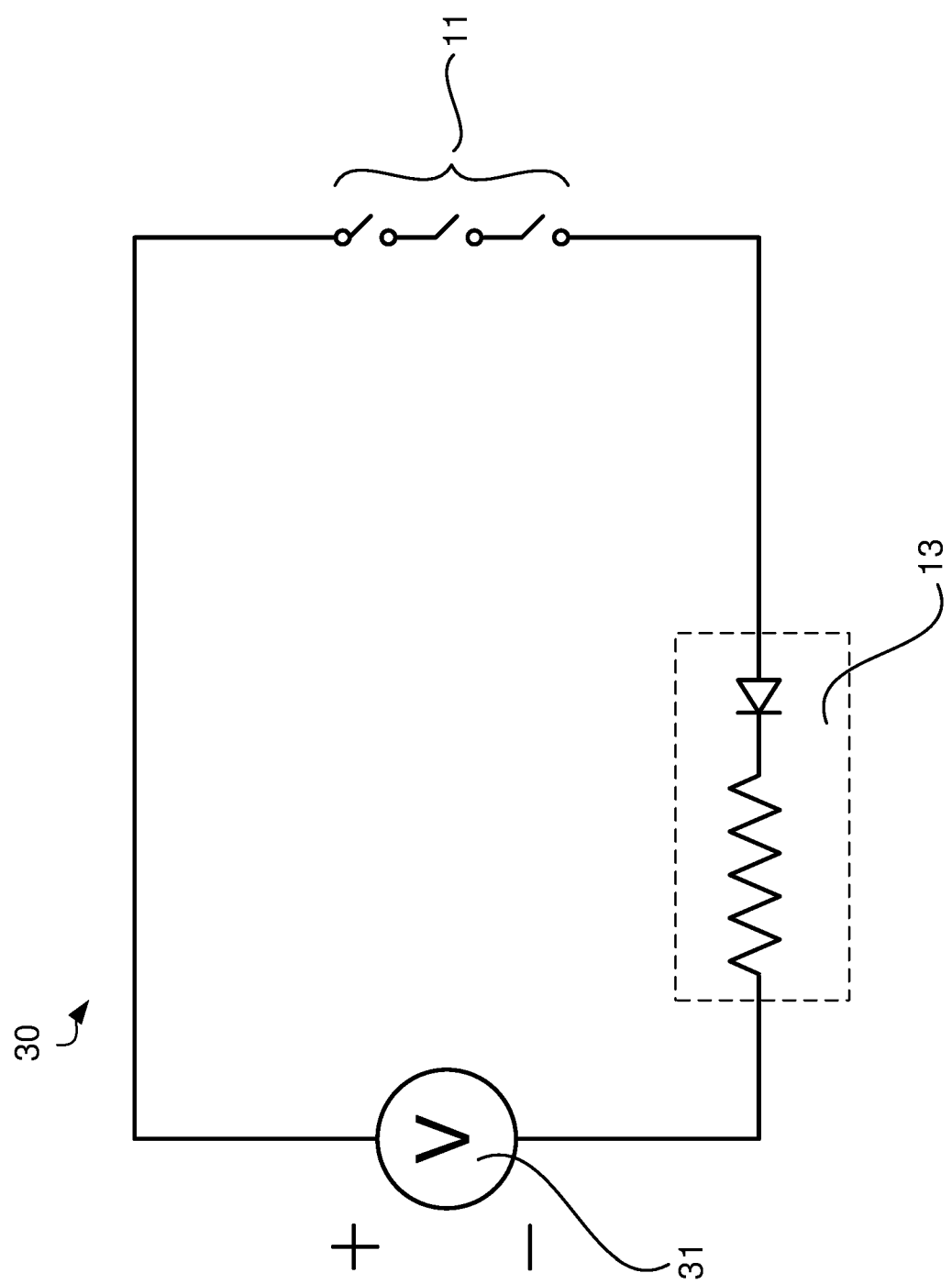
FIG. 3 illustrates a schematic of a circuit for a positioning guide system.

FIG. 3 illustrates a simplified schematic of circuit 30 for the positioning guide system 1. The circuit 30 includes a power source 31, a plurality of sensors 11 and a user interface 13. The power source 31 may be in the form DC supply, such as a battery. In this example, the sensors 11 are micro switches, which when the positioning guide 3 is positioned correctly, closes (completes) the electric circuit. The user interface 13 may be in the form of a light source (such as an LED) or an audio buzzer.

Thus when the positioning guide 3 is correctly positioned, the sensors 11 (in the form of micro switches) provide an output to the user interface 13. The user interface 13 may then produce a visual and/or audio output, such as a light or a buzzer, to inform the user that the positioning guide is correctly positioned.

In some examples, a haptic output may include an electromechanical agitator to provide the user output in the form of vibration that can be felt by the user. Examples may include an eccentric rotating mass actuator or a piezoelectric actuator.

The user interface 13 may be mounted on the positioning guide 3. This may assist the user to receive the user output. For example the user may be looking at the positioning guide 3 during the procedure. Therefore mounting the visual output at the positioning guide would assist the user receiving the output. Similarly, the user may be holding the positioning guide 3 and therefore the haptic user output 3 may be easily received by the user.

The above example of the user interface 13 is by example only. It is to be appreciated that in other examples, the sensors 11 may provide an output to a processing device. The processing device may receive the output to determine the relative position of the positioning guide 3 and the bone 9 and, if the position is not the correct position, determine a relative movement of the positioning guide 3 towards the correct position. For example, the user output may include an output to indicate to the user that the positioning guide should be moved towards one or more positions (e.g. left, right, up, down, back, forward, or any other suitable reference). In one example, this may be a spoken audio output, such as using a text-to-speech module to provide audio instructions. In another example, a visual display may provide a visual output to provide cues to the user. In yet another example, a plurality of lights may be provided on the positioning guide, wherein the lights are associated with respective sensors 11. The lights may be used to indicate the output of the respective one or more sensors 11 to assist the user to correctly position the positioning guide 3.

In another example, a visual representation of the positioning guide 3 positioned relative to the bone 9 may be generated and provided at a visual display. This may include a close up view of an area of interest, such as between the interface 5 and the plurality of anatomic landmarks. This allows the user to visualise the relative position to assist correct positioning. This may be advantageous during surgery, where the positioning guide 3 may be located such that it is difficult for the surgeon to see or where human tissue and other surgical tools obscure the view.

Method of Using the Positioning Guide System

An example of how the positioning guide system 1 may be used will now be described.

The positioning guide system 1 may be useful where patient specific shape matched guides are used for surgery. Examples include orthopaedic surgeries such as arthroplasty where bone 9 and/or cartilage may need to be reshaped or removed. This may include knee replacement surgery and hip replacement surgery.

Since the interface 5 of the positioning guide is configured for a particular patient, the anatomic landmarks 7 of the bone 9 and/or cartilage needs to be determined. This may include medical imaging, typically either CT or MRI. The output of the medical imaging process may be a series of individual greyscale images stored in the DICOM (Digital Imaging and Communications in Medicine) file format.

A three dimensional (3D) voxel map is built from the individual image slices. This is then filtered using a combination of selective Hounsfield values and other image segmenting techniques. An example of computer software that may be suitable for this step includes a product offered by Simpleware Ltd under the trade mark ScanIP. The filtered 3D voxel maps are then converted into a tessellated 3D model and transferred to CAD (Computer Aided Design) software using a Standard Tessellation Language.

The design of the body 6 of the positioning guide 3 is generated using CAD computer software. The 3D design is built relative to the patient's geometry by parametrically modifying a base model relative to key landmarks and a surgical plan. The patient's geometry may then be merged into the base model to form a patient specific design. An example of CAD software that may be suitable for this step includes a product offered by Dassault Systèmes SOLIDWORKS Corp. under the trade mark SOLIDWORKS. Another example of CAD software that may be suitable includes a product offered by Delcam Ltd under the trade mark PowerSHAPE.

The positioning guide 3 may then be manufactured as discussed above.

The positioning guide 3 will be accompanied by a patient specific reference model (of the bone 9 of the patient) which will be engraved with key landmarks and bone resection references. This reference model will also be used to validate the guide and sensors prior to intra operative placement. That is, the user or technician may test the suitability of the positioning guide 3 before surgery. This may assist in identifying design flaws and/or manufacturing defects and other faults etc. It may also allow the user to practice using the positioning guide 3 on the reference model before surgery.

Before surgery, the positioning guide system 1 may be sterilized. This may include autoclave and/or gamma irradiation of one or more components of the positioning guide system 1. In some examples different components may be sterilized with different processes and assembled together after sterilization. For example, the body 6 may be sterilized in an autoclave. The sensors 11 may include materials which would require gamma irradiation for sterilization. After sterilization, the sensors 11 may be mounted at the interface 5.

During surgery, the surgeon may perform the necessary procedures to expose the bone 9 and/or cartilage. The positioning guide 3 may then be positioned over the exposed portion of the bone 9 and/or cartilage. The user may attempt to move the positioning guide 3 to the correct position whilst receiving feedback in the form of the user output to indicate whether the positioning guide 3 is correctly positioned.

Once the user output indicates correct positioning, the positioning guide 3 may secured to the bone 9 and/or cartilage such as by insertion of pins through the pin apertures 19 described above.

The positioning guide 3 may then be used to guide surgical tools. For example a blade may be inserted through the guide aperture 21, whereby the guide aperture 21 limits the range of motion of the blade so that the blade only cuts specified portions of the bone 9. It is to be appreciated that the positioning guide 3 may be used to guide other forms of surgical tools.

Other Examples of a Positioning Guide

In the example illustrated in FIGS. 1 and 2, the positioning guide 3 is used for guiding a surgical tool, such a blade, to cut the femur bone in preparation for a replacement artificial knee. However, it is to be appreciated that the positioning guide system 1 and positioning guide 3 presently disclosed is not limited to use for a particular bone or bone joint. The body 6 of the positioning guide 3 may have an interface 5 for other bones 9.

Figure 4:
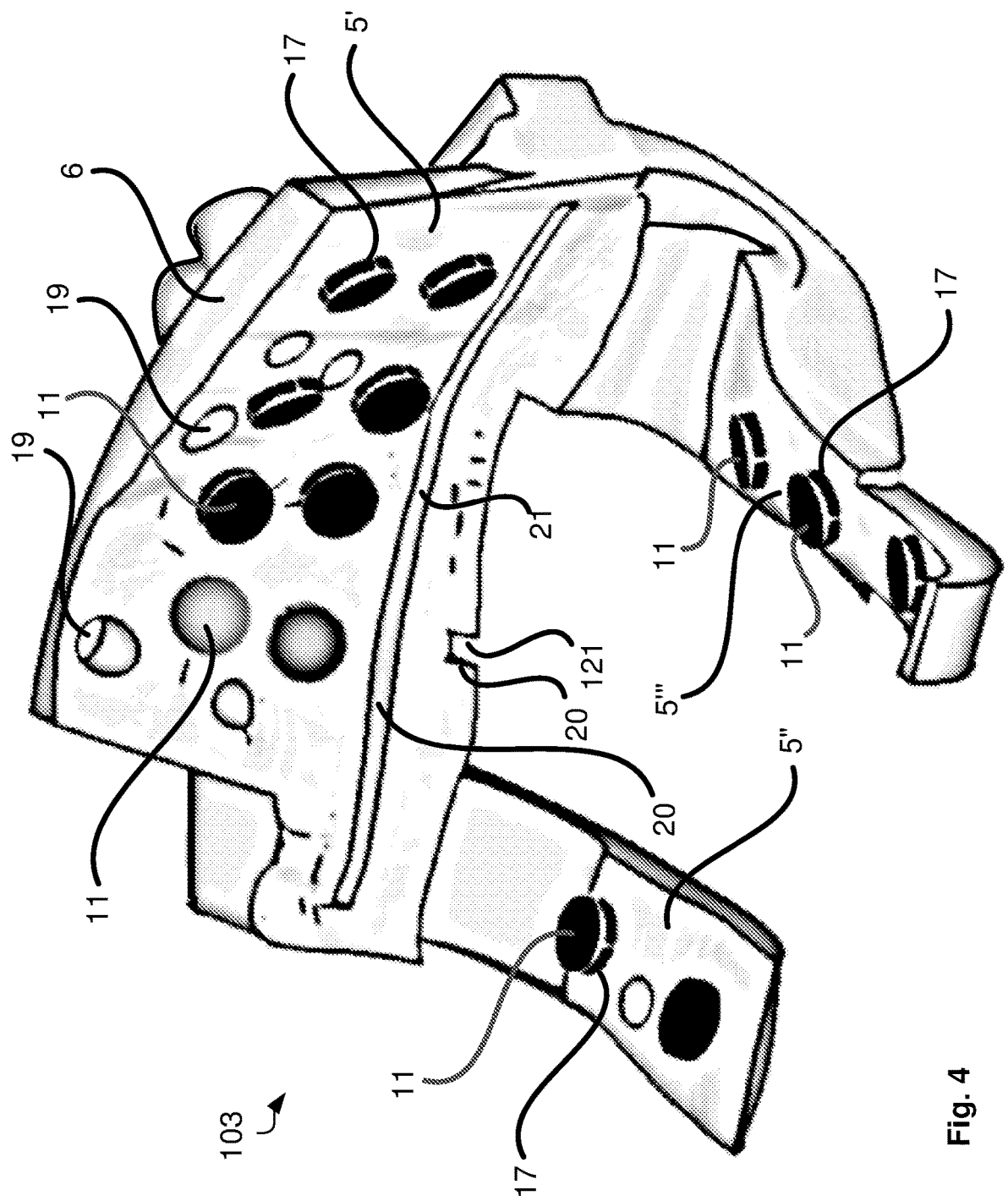
FIG. 4 illustrates a perspective view of a positioning guide for a tibia.
Figure 5:
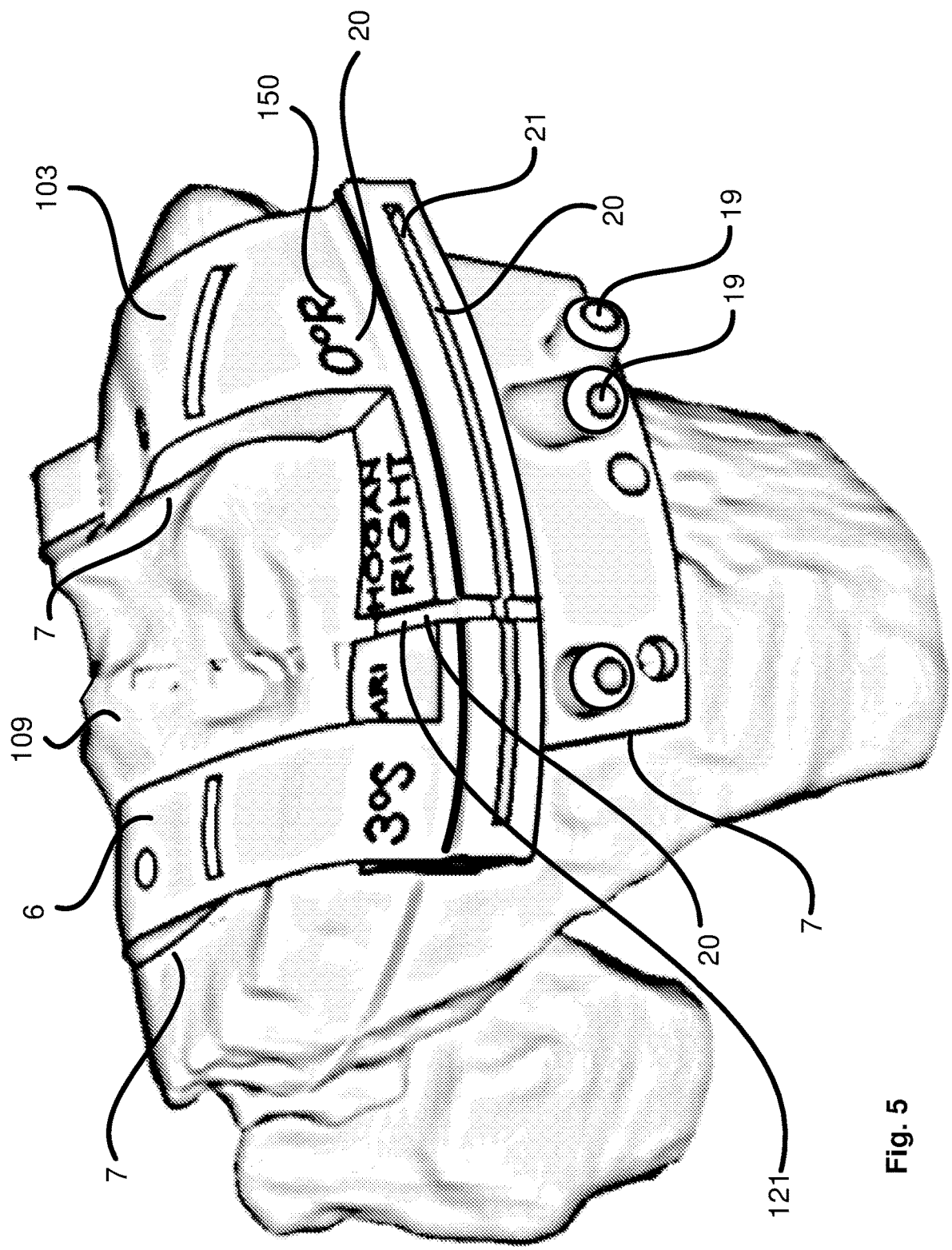
FIG. 5 illustrates a perspective view of the positioning guide in FIG. 4 positioned with a tibia.

FIGS. 4 and 5 illustrate another example of a positioning guide 103 that may be suitable for guiding surgical tools at the tibia bone 109 of a patient. In this example, like features from the above example are indicated with similar reference numerals. The interface in the positioning guide 103 includes three contoured surfaces 5', 5", 5''', where the three surfaces 5', 5", 5''' each have respective recesses 17 and sensors 11. The positioning guide 103 includes tool guides 20 in the form of a guide aperture 21 and an alignment reference channel 121. The alignment reference channel 121 may be used as an indexing surface for surgical tools. The positioning guide 103 further includes indicia 150 to indicate information in relation to the positioning guide 103. Such information may include information to assist in positioning surgical tools, identification information for the positioning guide, information to assist positioning of the positioning guide, identification and qualities of particular features of the positioning guide. For example, this may identify a guide aperture 21, alignment reference channel 121, pin aperture 19 as well as indicating indicate an angle or position of these features.

Figure 6:
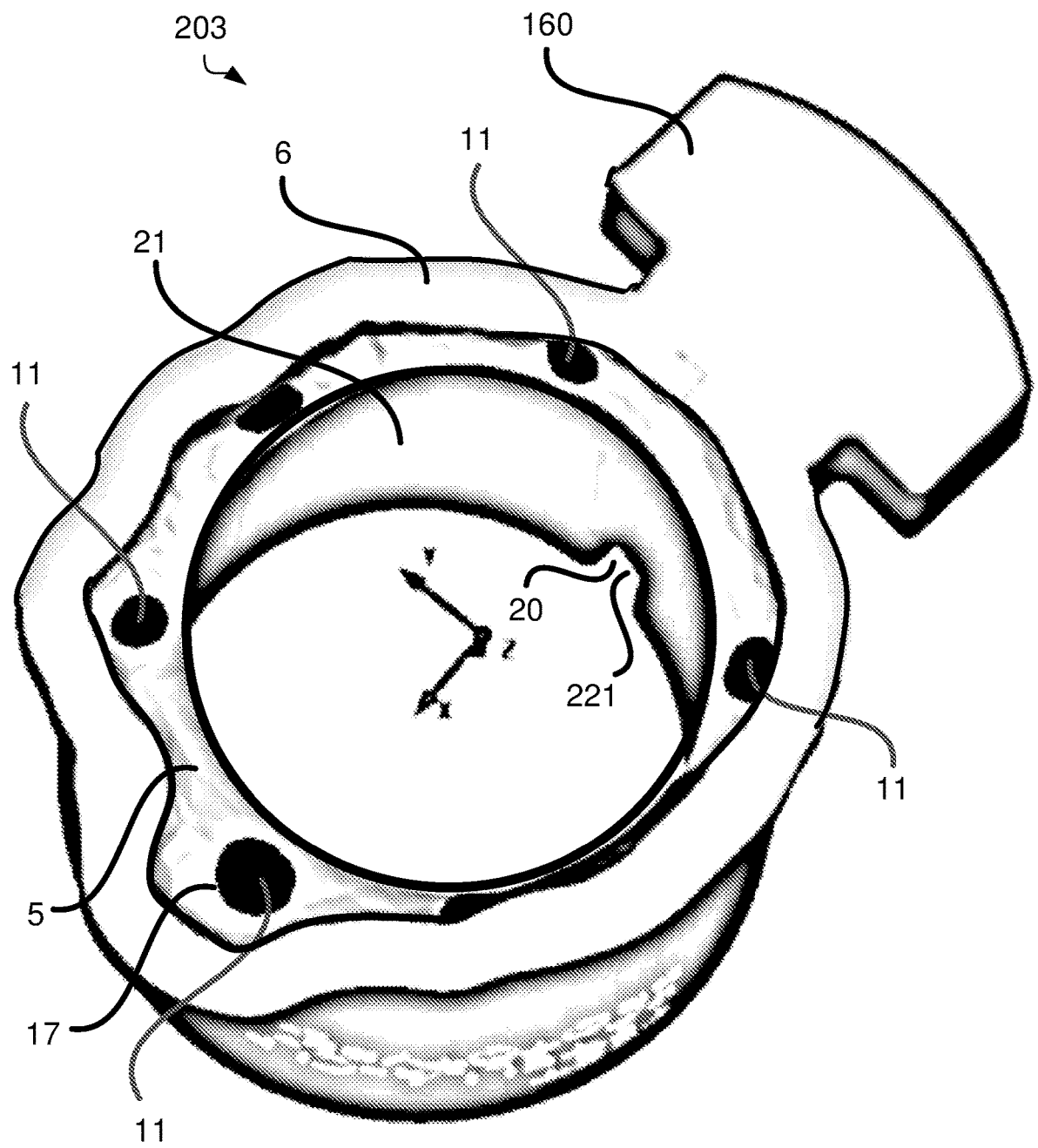
FIG. 6 illustrates a perspective view of a positioning guide for a patella.
Figure 7:
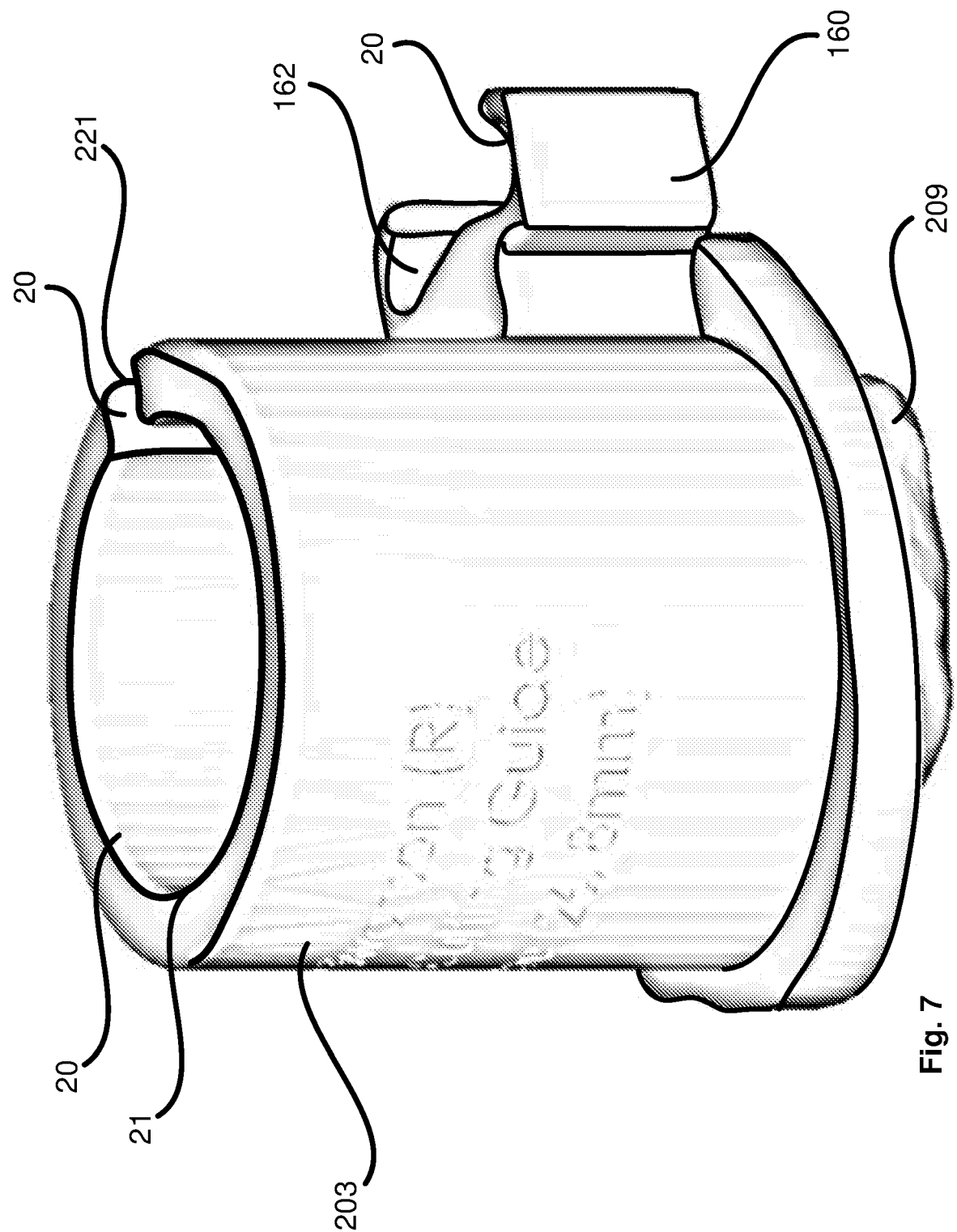
FIG. 7 illustrates a perspective view of the positioning guide in FIG. 6 positioned with a patella.
Figure 8:
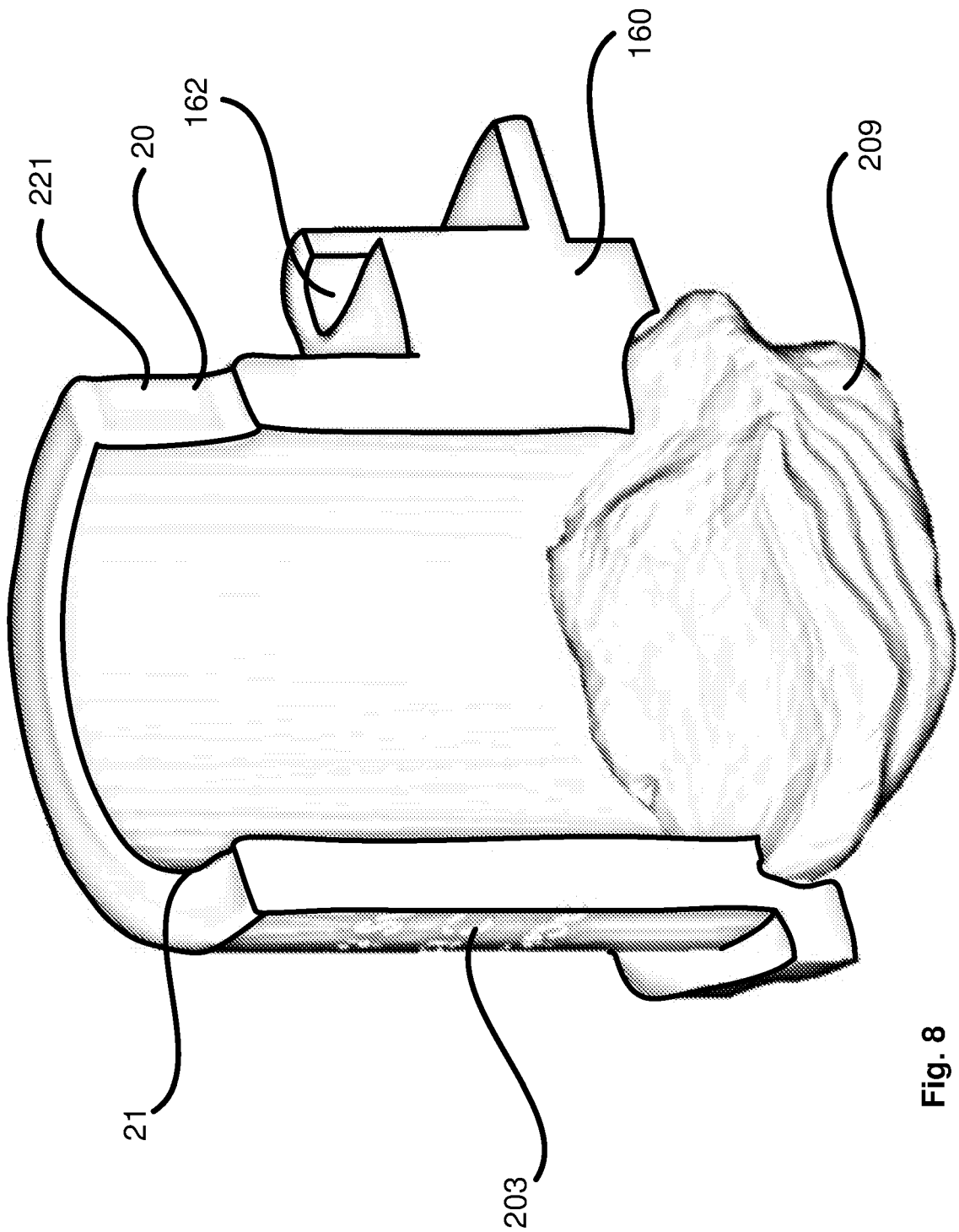
FIG. 8 illustrates a cross-section of the positioning guide in FIG. 6 positioned with a patella.

FIGS. 6, 7 and 8 illustrate another example of a positioning guide 203 that may be suitable for guiding surgical tools at the patella bone 209. In this example, the interface 5 includes an annular contoured surface where respective recesses 17 and sensors 11 are located. The guide aperture 21 passes through the annular interface 5, where the guide aperture 21 may receive a surgical tool. An alignment reference channel 221 may also be used as an indexing surface for surgical tools. The body 6 of the positioning guide 203 also includes a flange 160. The flange may assist handling of the positioning guide 203. The flange 160 further includes a slot 162. The slot 162 may be used to secure the positioning guide 203. Alternatively, the slot 162 may be used to secure other components such as a user interface 13.

Figure 9:
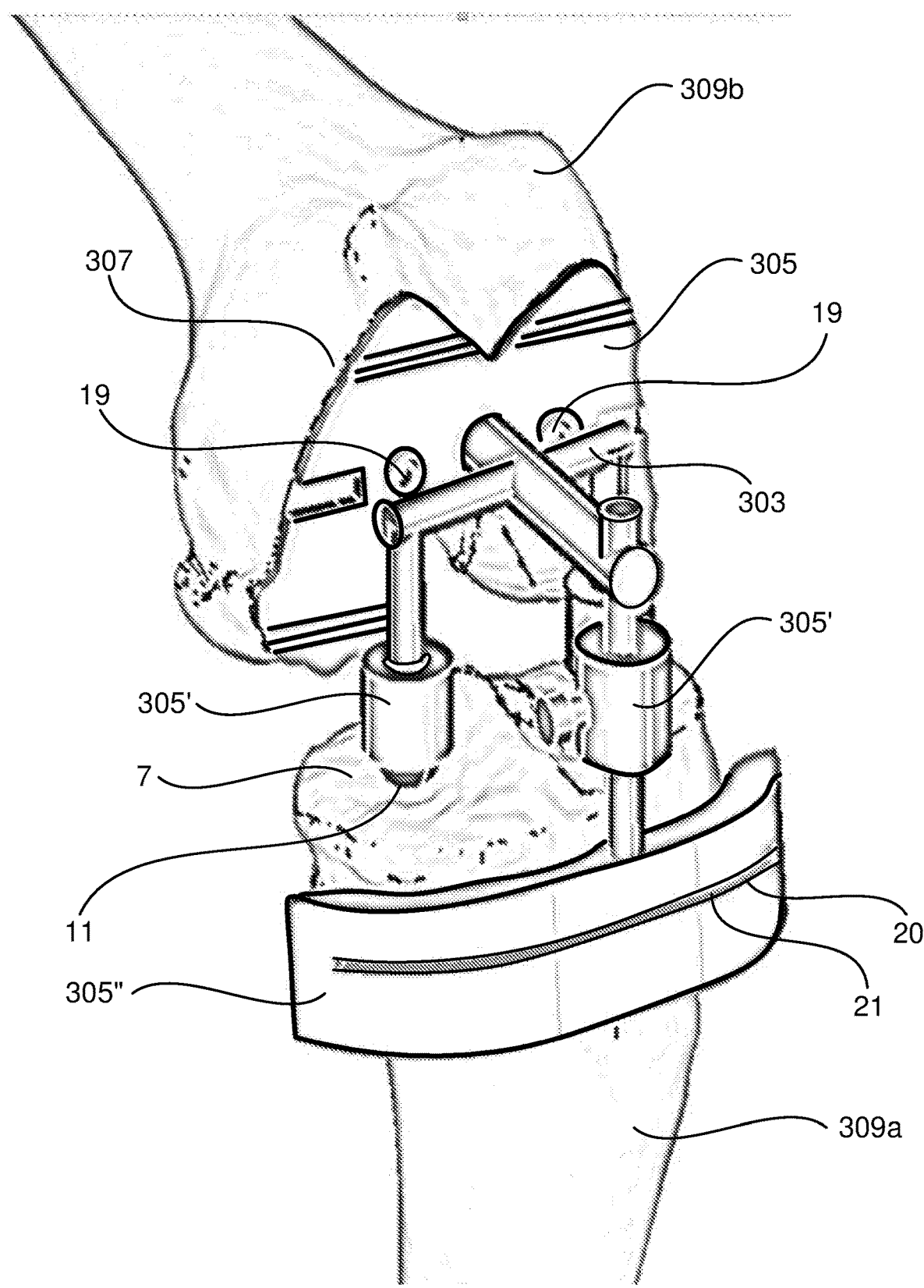
FIG. 9 illustrates a perspective view of a positioning guide for a tibia that is positioned with a tibia and a femur.
Figure 10:
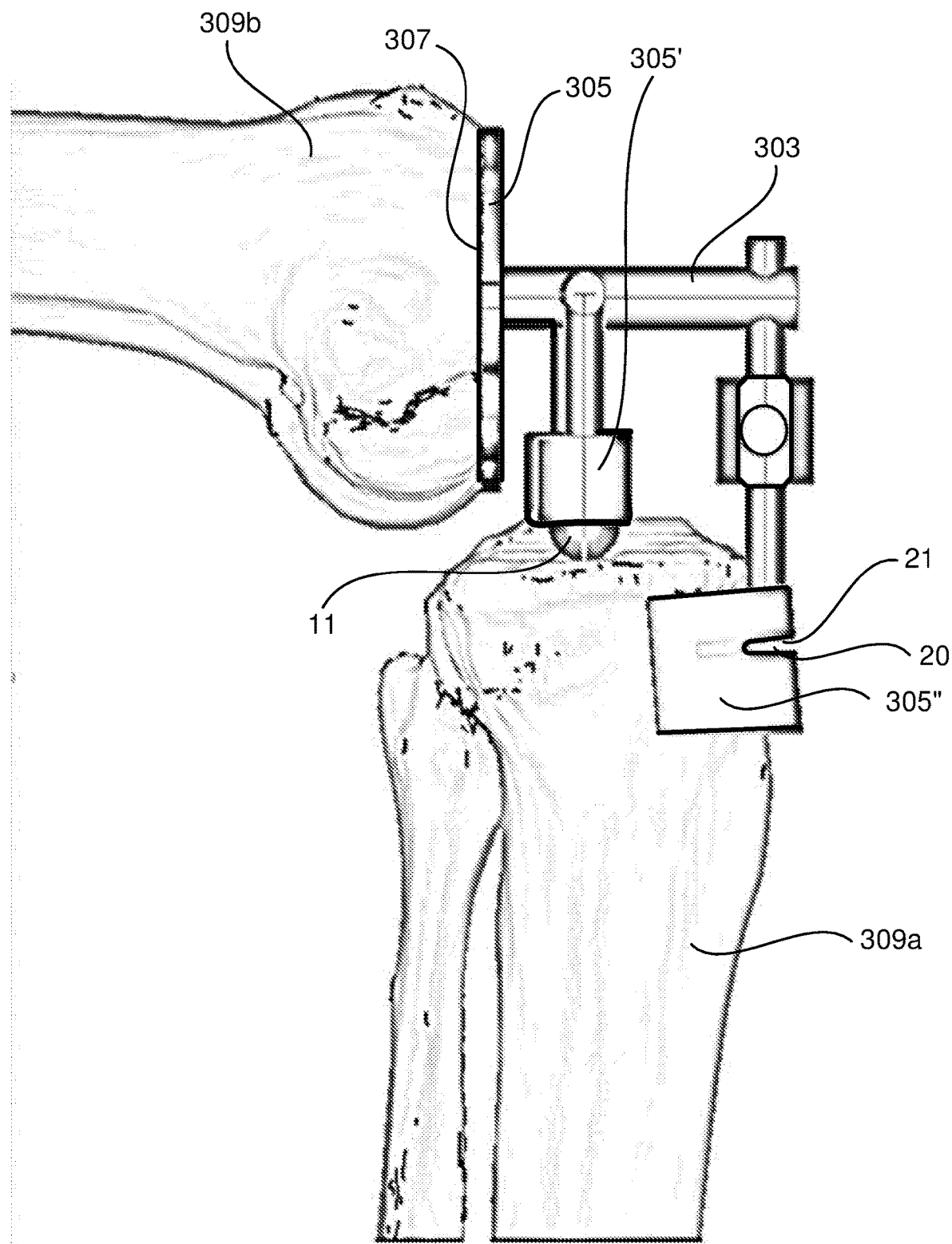
FIG. 10 is a side view of the positioning guide in FIG. 9.
Figure 11:
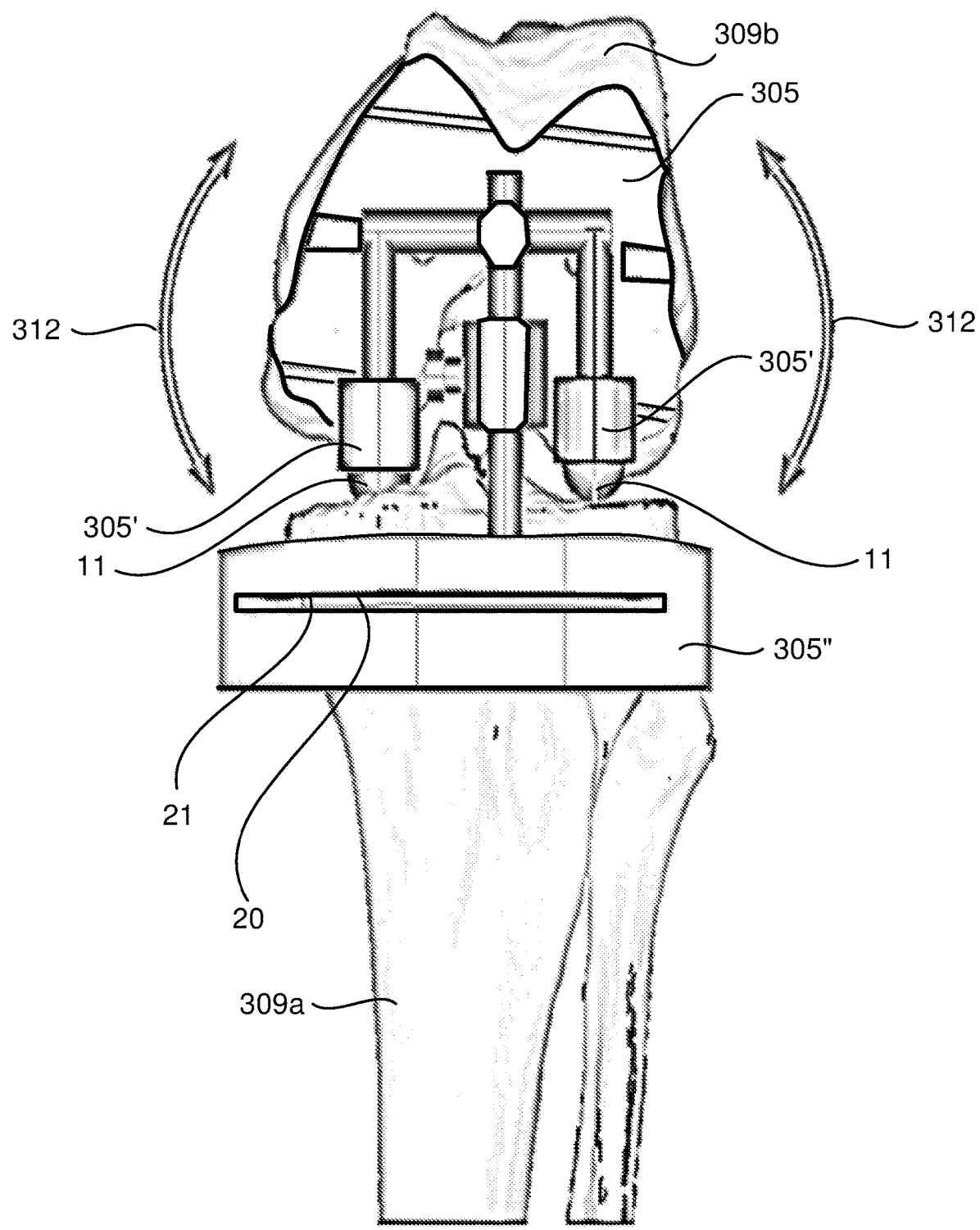
FIG. 11 is a front view of the positioning guide in FIG. 9.

FIGS. 9 to 11 illustrate another example of a positioning guide 303 that may be suitable for guiding surgical tools at the tibia bone 309a. In this example, the positioning guide 303 has an interface including a pair of point interfaces 305' and a curved contoured surface 305" to correspond to a plurality of anatomic landmarks 7 of the tibia bone 309a. In particular, the point interfaces 305' corresponds to anatomic landmarks at a top facing portion on the end of the tibia bone 309a. The curved contoured surface 305" corresponds to anatomic landmarks 7 at a forward facing potion of the end of the tibia bone 309a. The positioning guide 303 also includes a second interface 305 that is positioned relative to a second bone, cartilage and/or soft tissue constructs, which in this case is a prepared/cut surface 307 of an end of a femur bone 309b. Therefore the correct positioning of the positioning guide 303 includes a specified positioning relative to a plurality of bones, which in this case are the tibia bone 309a and the femur bone 309b.

The point interfaces 305', and the corresponding sensors 11, assist in positioning the positioning guide 303 relative to the tibia bone 309a. Referring to FIG. 11, the sensors 11 may assist in determining optimal alignment as indicated by arrows 312 in FIG. 11. It is to be appreciated that each point interface 305', in this example, only includes one corresponding sensor 11 and does not have a contoured surface extending between the two sensors 11.

The curved contoured surface 305" may be shaped to correspond to the anatomic landmarks, in particular, a surface of the forward facing portion of the end of the tibia bone 309a. In some examples, this surface may include sensors 11 similar to sensors described in the example of FIGS. 4 and 5. In other examples, the curved contoured surface 305" may not include sensors.

The second interface 305 includes a flat contact surface for positioning against second anatomic landmarks, in the form of a flat prepared surface of a femur bone 309b. The second interface 305 includes pin apertures 19 to allow a fastener to pass through to secure the second interface 305 relative to the femur bone 309b. The fasteners may pass into respective apertures created in a previous procedure. In another example, guide pins may be inserted into apertures in the femur bone 309b, and the guide pins are in turn received by the pin apertures 19 of the second interface 305.

In one example, the flat prepared surface of the femur bone 309b may be prepared according to the example of FIGS. 1 and 3 described above. In some examples, the flat prepared surface of the femur bone 309b may have been prepared during a previous surgical procedure. For example, the patient may have knee replacement surgery previously, and the positioning guide 303 is used for revision surgery where bone/cartilage needs to be prepared for a subsequent knee replacement surgery. Accordingly in further examples, sensors may be provided to produce an output indicative of the proximity of the interface to one or more landmarks that are part of an existing implanted device.

In other examples, the interface (and/or second interface 305) may be positioned relative to an existing implanted device. The existing implanted device would, in turn, be positioned relative to anatomic landmarks of the patient. For example, the second interface 305 may be positioned and secured to part of an existing replacement joint (which in turn is secured and positioned to respective part(s), that may include anatomic landmarks, of the patient). After using the existing replacement joint to assist in positioning the positioning guide 3, the existing replacement joint (or parts thereof) may be removed.

It is also to be appreciated that in some alternatives, the anatomic landmarks of the patient may include surfaces of human tissue that have been previously shaped or prepared. For example, the flat prepared surface of the femur bone 309b may, in some examples, form at least part of an anatomic landmark. Therefore in one alternative, the second interface 305 may also include sensors 11 to provide an output indicative of the proximity of the second interface 305 to the flat prepared surface of the femur bone 309b.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A positioning guide system for guiding a surgical bone preparation tool comprising:
   a positioning guide comprising:
      a patient specific interface having a contoured surface that corresponds to, and to uniquely face, a plurality of patient specific anatomic landmarks of a patient;
      a plurality of sensors exposed at the contoured surface to provide an output indicative of proximity or pressure between the patient specific interface and one or more of the plurality of patient specific anatomic landmarks; and
      a tool guide, to receive a surgical tool, positioned relative to the patient specific interface;

a processing device configured to:
- determine, based on the output of the plurality of sensors, whether the positioning guide is in a correct and unique position relative to the patient specific anatomic landmarks; and
- if the positioning guide is in an incorrect position relative to the patient specific anatomic landmarks, determine relative movement required to move the positioning guide to the correct and unique position; and a user interface to provide a user output indicative of: (i) correct and unique positioning of the positioning guide relative to the patient specific anatomic landmarks; and (ii) if in the incorrect position, the relative movement required to move the positioning guide to the correct and unique position.

2. The positioning guide system according to claim 1, further comprising a plurality of recesses at the patient specific interface to receive the plurality of sensors.

3. The positioning guide system according to claim 1, wherein the plurality of sensors are mounted to the patient specific interface.

4. The positioning guide system according to claim 1, wherein the plurality of sensors include pressure sensors wherein the output is indicative of the pressure between the patient specific interface and the patient specific anatomic landmarks.

5. The positioning guide system according to claim 1, wherein the sensors include proximity sensors wherein the output is indicative of distance between the patient specific interface and the patient specific anatomic landmarks.

6. The positioning guide system according to claim 1, wherein the tool guide comprises one or more guide apertures to receive a surgical tool.

7. The positioning guide system according to claim 1, wherein the user output includes one or more of a visual, audio and haptic output.

8. The positioning guide system according to claim 1, wherein the user interface is mounted to the positioning guide.

9. The positioning guide system according to claim 1, wherein the contoured surface is contoured to correspond to anatomic landmarks on a femur, tibia or patella of the patient.

10. The positioning guide system according to claim 1, wherein the plurality of anatomic landmarks comprise features of a first bone, cartilage and/or soft tissue constructs of the patient.

11. The positioning guide system according to claim 10, wherein the tool guide provides a reference for the surgical tool relative to the first bone, cartilage and/or soft tissue constructs of the patient.

12. The positioning guide according to claim 10, wherein the tool guide provides a reference for the surgical tool relative to a second bone, cartilage and/or soft tissue constructs of the patient.

13. The positioning guide system according to claim 1, wherein the positioning guide includes a second patient specific interface to correspond to second anatomic landmarks, separate to the said patient specific anatomic landmarks, wherein correct positioning of the positioning guide further comprises positioning the second patient specific interface relative to the second anatomic landmarks.

14. The positioning guide system according to claim 13, wherein the second anatomic landmarks include a surgically prepared surface of a further bone, cartilage and/or soft tissue constructs.

15. The positioning guide system according to claim 1, wherein the processing device is further configured to:
- determine the relative position of the positioning guide and the patient specific anatomic landmarks;
- wherein the user interface is further configured to provide a provide a visualisation of the relative position of the positioning guide and the patient specific anatomic landmarks.

16. A positioning guide for guiding a surgical tool, the positioning guide comprising:
- a patient specific interface having a contoured surface that corresponds to, and to uniquely face, a plurality of patient specific anatomic landmarks of a patient;
- a plurality of sensors exposed at the contoured surface to provide an output indicative of proximity or pressure between the patient specific interface and one or more of the plurality of patient specific anatomic landmarks; and
- a tool guide, to receive a surgical tool, positioned relative to the patient specific interface,
- wherein the output is further indicative of a relative position of the positioning guide and the patient specific anatomic landmarks.

17. A positioning guide system for guiding a surgical bone preparation tool comprising:
- a positioning guide comprising:
  - a patient specific interface having a contoured surface that corresponds to, and to uniquely face, a plurality of patient specific anatomic landmarks of a patient; and
  - a plurality of sensors exposed at the contoured surface to provide an output indicative of proximity or pressure between the patient specific interface and one or more of the plurality of patient specific anatomic landmarks; and
  - a tool guide, to receive a surgical tool, positioned relative to the patient specific interface;
- a processing device configured to determine a relative position of the positioning guide to the patient specific anatomic landmarks, and
- a user interface to provide a user output indicative of the relative position of the positioning guide to the patient specific anatomic landmarks.

* * * * *